(12) United States Patent
Nair et al.

(10) Patent No.: US 7,217,355 B2
(45) Date of Patent: May 15, 2007

(54) $NO_x$ GAS SENSOR METHOD AND DEVICE

(75) Inventors: Balakrishnan G. Nair, Sandy, UT (US); Jesse A. Nachlas, Salt Lake City, UT (US); Michael Middlemas, Murry, UT (US)

(73) Assignee: Ceramatec, Inc., Salt Lake City, UT (US)

( * ) Notice: Subject to any disclaimer, the term of this patent is extended or adjusted under 35 U.S.C. 154(b) by 0 days.

(21) Appl. No.: 11/137,693

(22) Filed: May 25, 2005

(65) Prior Publication Data

US 2006/0027465 A1 Feb. 9, 2006

Related U.S. Application Data

(60) Provisional application No. 60/574,622, filed on May 26, 2004.

(51) Int. Cl.
*G01N 27/407* (2006.01)
(52) U.S. Cl. .............. 205/781; 204/424; 204/429; 73/23.31
(58) Field of Classification Search ............. 205/781, 205/785; 204/424, 426, 429; 73/23.31
See application file for complete search history.

(56) References Cited

U.S. PATENT DOCUMENTS 3,843,400 A * 10/1974 Radford et al. ............. 429/152
4,358,950 A * 11/1982 Chang ....................... 73/31.05
5,897,759 A   4/1999 Kurosawa et al.
6,019,881 A   2/2000 Kurosawa et al.
6,071,393 A * 6/2000 Oshima et al. ............. 204/425
6,126,902 A   10/2000 Kunimoto et al.
6,143,165 A   11/2000 Kurosawa et al.
6,287,439 B1 * 9/2001 Kato et al. ................. 204/425
6,303,011 B1   10/2001 Gao et al.
6,319,377 B1   11/2001 Hasei et al.
6,533,911 B1 * 3/2003 Fujita et al. ............... 204/424
6,551,497 B1   4/2003 Gao et al.
6,764,591 B1   7/2004 Dutta et al.
6,773,565 B2 * 8/2004 Kunimoto et al. .......... 204/425
2002/0017461 A1   2/2002 Kunimoto et al.

* cited by examiner

*Primary Examiner*—Kaj K. Olsen
(74) *Attorney, Agent, or Firm*—David Fonda

(57) ABSTRACT

The present invention is a method and apparatus for measuring the total $NO_x$ concentration in a gas stream utilizing the principles of a $NO_x$ sensor, i.e., mixed potential sensor. The exhaust gas is first conditioned by a catalyst assembly that converts the various species of nitrogen oxide gases present to a fixed steady state concentration ratio of $NO_2$/NO, where $NO_2$ is approximately 0–10% of the total $NO_x$ concentration present in the gas exhaust, thereby enabling the $NO_x$ sensor to generate a meaningful and reproducible determination of the concentration of total $NO_x$ present in the gas being measured. The catalyst assembly also functions to oxidize any unburned combustibles such as $CH_4$, CO, etc., and remove potential contaminants such as $SO_2$.

67 Claims, 3 Drawing Sheets

$NO_x$ GAS SENSOR METHOD AND DEVICE

RELATED APPLICATIONS

This application claims priority to U.S. Provisional Patent Application No. 60/574,622, filed May 26, 2004, and is incorporated by reference herein.

TECHNICAL FIELD

The present invention relates in general to the measurement of $NO_x$ gases in exhaust streams generated from the combustion of hydrocarbons and particularly the combustion of diesel fuels in cars and trucks.

BACKGROUND OF THE INVENTION

One known $NO_x$ sensor is configured as a flat plate multilayer ceramic package design that includes two or more chambers. In the first chamber there are electrodes attached to an oxygen ion conducting electrolyte membrane, thereby forming an oxygen pump to remove the oxygen. In addition, $NO_2$ is decomposed to NO and one-half $O_2$. The free oxygen is removed in the first chamber so that theoretically the only gas that enters the second chamber is NO. Another oxygen pump is in the second chamber and is a NO decomposing element that removes the oxygen from the NO. The electrical current produced from the decomposition of NO and the transport of oxygen is correlated to the NO concentration.

There are a number of concerns that affect the commercial application of this known $NO_x$ sensor. For example, when the $NO_x$ concentration to be detected is low, there is significant interference from the residual oxygen. In addition, the signal current is very small, thus making it susceptible to electronic noise commonly found in an automobile. Also, the exhaust gas typically has pulsations in the flow rate caused by cylinder firings that influence the ability of the oxygen pump to effectively remove all of the free oxygen and may result in measurement error. This device may also contain a small diffusion hole that limits the passage of gas into the measurement chambers and is prone to clogging.

Another known $NO_x$ sensor utilizes a similar flat plate multilayer ceramic package design. There are a few significant differences in the operation principle for this sensor; namely, the sensor is a mixed potential type rather than amperometric, and the use of the first chamber is for converting NO to $NO_2$ and vice versa. It is a well established phenomenon of mixed potential $NO_x$ sensors that the voltage signal generated from the gas species NO and $NO_2$ are of opposite sign, thereby making it difficult to distinguish a meaningful voltage signal in the presence of both gases. Some sensors have attempted to overcome this problem by utilizing the flat plate multilayer package type design with two separate chambers built into the design. Attempts have also been made to convert all of the $NO_x$ gas species into a single species with the use of an electrochemical oxygen pump that pumps oxygen into the first chamber—thereby converting all of the gas to $NO_2$—or conversely by removing oxygen from the chamber and reducing all of the $NO_2$ to NO. This conditioned gas then passes into the second chamber where the $NO_x$ concentration is measured by the voltage signal generated from a mixed potential type sensor.

There are a number of limitations to this approach that have hampered the commercialization of this configuration. One significant concern is the reproducibility of the conversion system to completely convert all the $NO_x$ gases into a single species under varying gas concentration conditions. In addition, the oxygen pump conversion cell tends to degrade with time, further contributing to the issue of reproducibility. Because the effects of these concerns are magnified in the low concentration range, this measurement approach is not well suited for detecting low concentrations of $NO_x$ gases.

Additional drawbacks common to both of the sensor mechanisms disclosed above stem from the fundamental design of the flat plate ceramic multilayer system. Response times tend to be slow because of the complexity of the device where gas first enters a diffusion port, is conditioned in a first chamber, and then diffuses into a second chamber. Achieving rapid gas exchange that can keep up with the dynamic environment of the engine exhaust is difficult to achieve in these configurations. Also, the corrosiveness of the gas—along with fine particulates—may result in the clogging of the diffusion controlling port, or at the very least, changes in the gas flow dynamics with time. Finally, the pulsations in the gas flow rates due to cylinder firings and the accompanying electrical noise typical of automobiles make it difficult to control and monitor the low voltage and current circuits associated with these devices.

Another known $NO_x$ sensor utilizes a zeolite catalyst to condition the gas prior to being measured by the sensor. Although this catalyst has been demonstrated to be effective in controlled gas environments, no data has been reported wherein the catalyst has suitably performed in $H_2O$ containing gases. Exhaust gases from combustion processes such as diesel exhaust always contain some $H_2O$ vapor as this is one of the major chemical byproducts of combustion of hydrocarbon fuels along with $CO_2$. As such, the utilization of the $NO_x$ sensor incorporating a zeolite catalyst in such applications is limited because of the catalyst's well known instability in the presence of $H_2O$.

The present invention is provided to address these and other considerations.

SUMMARY OF THE INVENTION

The present invention is directed to a method and apparatus for determining $NO_x$ concentration of an exhaust gas. The apparatus comprises an input assembly capable of receiving the exhaust gas and producing a conditioned gas output. The input assembly includes at least three of the following stages: a stage including a catalyst structure for converting $NH_3$ in the exhaust gas to $N_2$ and $H_2O$; a stage including a catalyst structure for absorbing $SO_2$ or $H_2S$ from the exhaust gas; a stage including a catalyst structure for oxidizing unburned hydrocarbons and gases to higher oxidation states; and a stage including a catalyst structure to establish a steady state equilibrium concentration ratio between NO and $NO_2$. A $NO_x$ sensor is operably connected to the input assembly and receives the conditioned gas output of the input assembly wherein the concentration of the total $NO_x$ present can be determined.

A further aspect of the present invention includes the $NO_x$ sensor including a mixed potential sensor receiving the conditioned gas output and generating a voltage signal being a function of the concentration of the total $NO_x$ present.

Another aspect of the present invention includes the $NO_x$ sensor including a porous semi-conductive layer capable of absorbing $NO_x$ gases wherein a physical property is monitored to determine the concentration of $NO_x$ present.

A still further aspect of the present invention includes an oxygen senor. The oxygen sensor and the $NO_x$ sensor cooperate to determine the $NO_x$ concentration in the exhaust gas.

Yet another further aspect of the present invention includes an electronic system utilizing a formula and capable of calculating the $NO_x$ concentration of the exhaust gas based on a measured oxygen concentration. The electronic system can include a database and a data table, wherein the electronic system, database, or data table cooperate to determine the $NO_x$ concentration of the exhaust gas as a function of oxygen concentration An object of the present invention is to overcome the problems commonly associated with mixed potential $NO_x$ sensors and to provide a sensor useful for measuring total $NO_x$ concentration in an exhaust gas stream.

Another object of the present invention is to provide a catalyst assembly that conditions the exhaust gas prior to entering the sensor(s) whereby the ratio of $NO_2/NO$ is in the range of 0.01–0.10.

A further object of the invention is to provide an accurate and reproducible voltage signal that correlates to the total $NO_x$ concentration in the exhaust gas.

A still further object of the present invention is to oxidize any unburned combustibles, e.g., $C_3H_6$, $CH_4$, CO, etc; that are typical of an exhaust gas stream, and to remove or reduce the concentration of gases such as $SO_2$ or $H_2S$ that may interfere with the lifetime performance of the electrode(s) and/or sensor.

Another further object of the present invention is to provide a sensor that is capable of measuring $NO_x$ concentration as low as 1 ppm.

Yet another object of the present invention is to incorporate an oxygen sensor within the body of the $NO_x$ sensor so that oxygen and $NO_x$ concentrations can be measured simultaneously; thereby enabling the accurate determination of the total $NO_x$ concentration that is a function of the oxygen concentration.

A still further object of the present invention is to provide a voltage output signal that is not influenced by other gas constituents in the exhaust gas, e.g., hydrocarbons, CO, $CO_2$, $SO_2$, $H_2$, $NH_3$, and $H_2O$.

Yet a still further object of the present invention is to provide a $NO_x$ sensor having a voltage output signal that is not significantly affected by the presence of $SO_2$ concentrations up to 100 ppm, and preferably below 15 ppm.

And yet another object of the present invention is to provide a $NO_x$ sensor capable of measuring total $NO_x$ concentration in the range of 0.1–1500 ppm, and preferably from 1–1500 ppm.

Other advantages and aspects of the present invention will become apparent upon reading the following description of the drawings and detailed description of the invention.

DETAILED DESCRIPTION OF THE INVENTION

Figure 1:
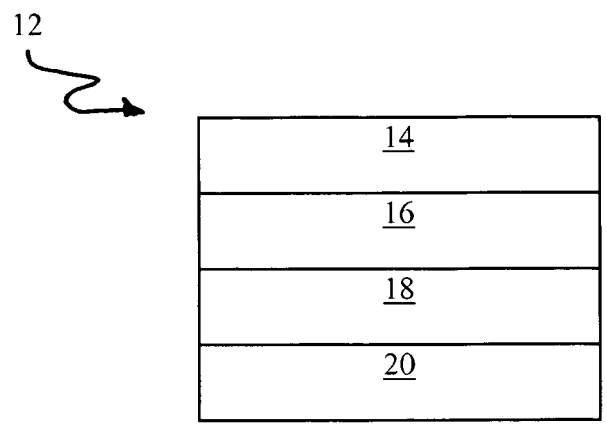
FIG. 1 is a schematic representation of one embodiment of the input assembly of the present invention.

While the present invention is capable of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

One embodiment of the present invention is directed to a method and apparatus for determining $NO_x$ concentration of an exhaust gas. An apparatus 10 comprises an input assembly 12 (shown in FIG. 1) capable of receiving the exhaust gas and producing a conditioned output gas. The input assembly 12 includes at least three of the following four stages: a first stage 14 including a first catalyst structure for converting $NH_3$ in the exhaust gas to $N_2$ and $H_2O$ (to prevent cross sensitivity); a second stage 16 including a second catalyst structure having an absorbent material for absorbing $SO_2$ from the exhaust gas; a third stage 18 including a third catalyst structure for oxidizing unburned hydrocarbons (and ammonia) and gases to higher oxidation states; and, a fourth stage 20 including a fourth catalyst structure for establishing a steady state equilibrium concentration ratio between NO and $NO_2$. In one embodiment, the first catalyst structure of the first stage 14 comprises a catalyst material from the group consisting of Cu, Ag, $NiAl_2O_4$, $MnO_2$, $V_2O_5$, and any mixture thereof. It is to be understood that the sequence of stages within the input assembly 12 is not limited to any specific order.

Figure 2:
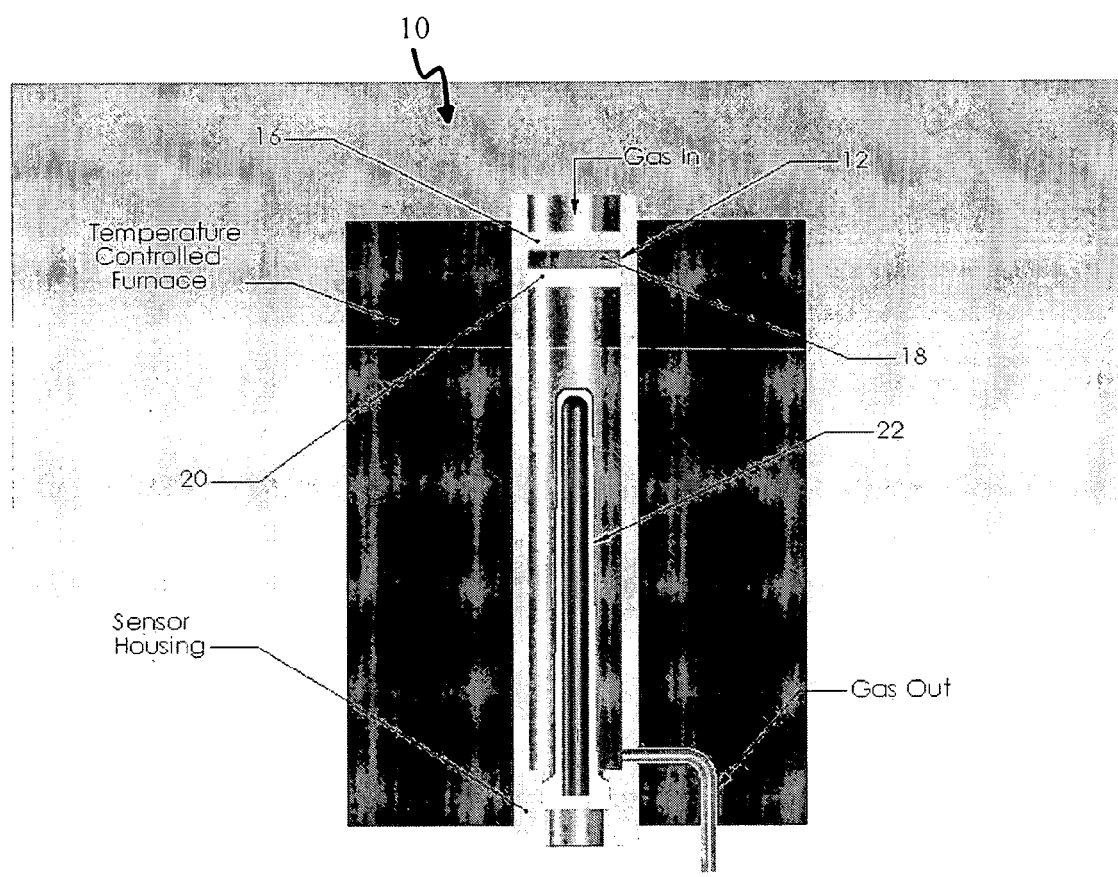
FIG. 2 is a schematic representation of one embodiment of the present invention.

FIG. 2 depicts a preferred embodiment of the present invention to achieve an accurate measurement of total $NO_x$ concentration in a gas stream. A $NO_x$ sensor 22 is operably connected to the input assembly 12 and receives the conditioned output gas from the input assembly wherein the concentration of the total $NO_x$ present can be determined. In this embodiment, the exhaust gas passes through a three-stage input assembly 12. The initial stage 16 shown in FIG. 2 includes a catalyst structure including an absorbent material such as CaO, MgO, or a compound from the spinel or perovskite group of materials that serve the function of removing $SO_2$ from the exhaust gas stream. The absorbent material can be in the form of a packed pellet or infiltrated support that may be periodically replaced during servicing without disassembling the rest of the apparatus 10.

The catalyst structure of the next stage 18 of the input assembly 12 shown in FIG. 2 includes an oxidation catalyst, e.g., $RuO_2$ or $CoO_2$, which functions to oxidize unburned hydrocarbons and convert CO to $CO_2$. The final stage 20 of the input assembly 12 shown in FIG. 2 a catalyst structure including a silver metal configured as a mesh or a coating on a ceramic substrate that acts to establish a steady state concentration ratio between NO and $NO_2$ wherein the $NO_2$ percentage of the total $NO_x$ gas present is in the range of 0–5% optimally, and at least within the range of 0–10%.

Figure 3:
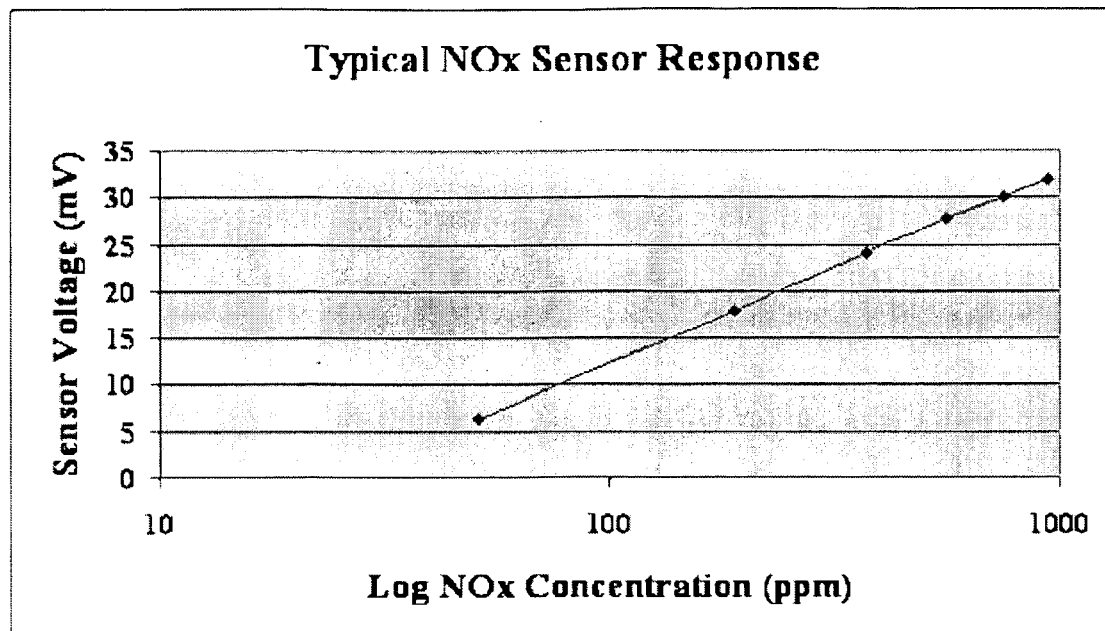
FIG. 3 is a graph of data obtained using the embodiment shown in FIG. 2 that demonstrates the relationship between $NO_x$ concentration and the voltage signal generated by the sensor.
Figure 4:
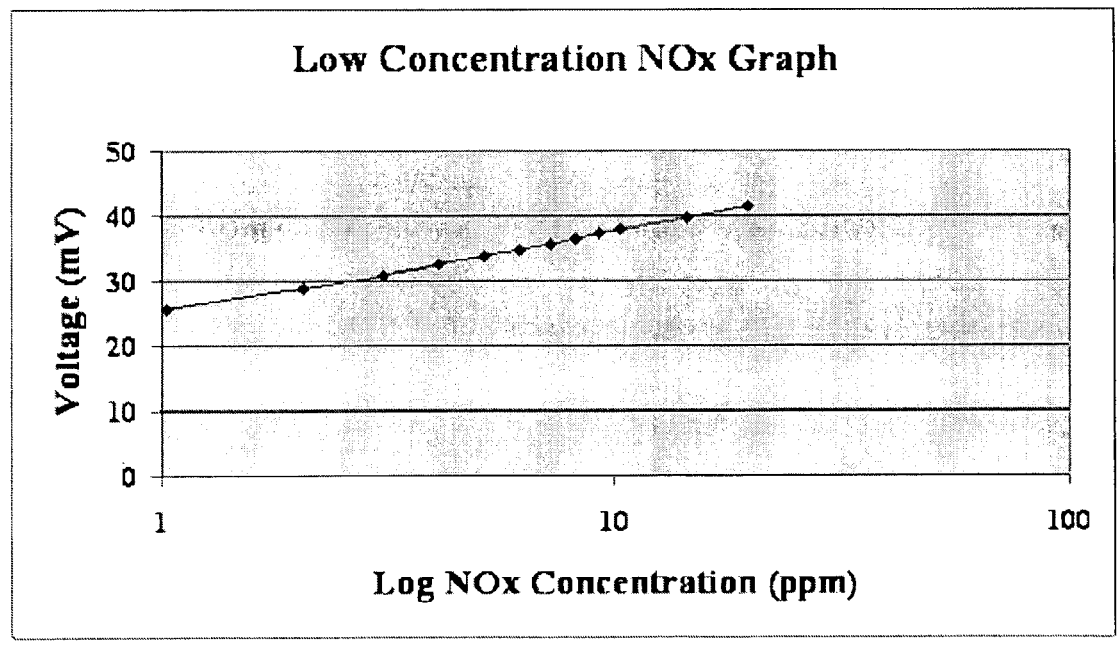
FIG. 4 is a plot of the voltage signal generated with varying concentrations of $NO_x$ gas in the low concentration range of 1–20 ppm.

After the exhaust gas has been conditioned by the input assembly 12, it passes to a $NO_x$ Sensor cavity, i.e., a mixed potential sensor 22, wherein a mixed potential voltage signal is generated. In one embodiment, the mixed potential sensor includes a metallic sensing electrode. The metallic sensing electrode includes an electrolyte material having a range of approximately 10–40 vol. %. In one embodiment, the electrolyte material is approximately 15–25 vol. %. The electrolyte material may comprise a doped zirconia material, or one of the following: ceria, gadolinia, hafnia, thoria, bismuth oxide, or any mixture thereof. The mixed potential voltage signal is a function of the concentration of the total $NO_x$ present. FIGS. 3 and 4 depict typical graphs of voltage with respect to the logarithm of the total $NO_x$ concentration—in the range of 10–1000 ppm (FIG. 3) and 1–20 ppm (FIG. 4) 13 and is independent of the $NO_x$ gas species that enter the apparatus 10.

In some modifications of the present invention, the voltage signal will be proportional to the logarithm of the $NO_x$ concentration; while it may also be possible to construct the apparatus such that in the low $NO_x$ concentration range, e.g., 1–30 ppm, the voltage output signal will be directly proportional to the $NO_x$ concentration, i.e., linear dependence.

Figure 6:
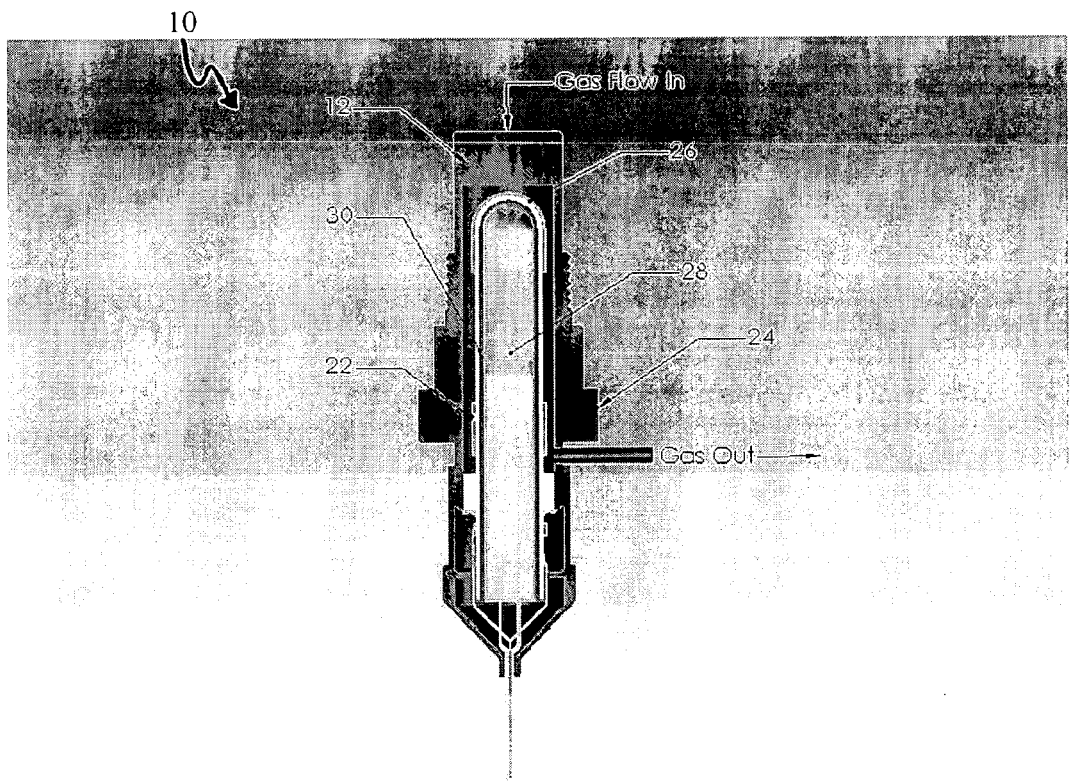

In another embodiment of the present invention, an oxygen sensor 26 is incorporated with the apparatus 10. Referring to FIG. 6, the oxygen sensor 26 is configured within the housing 24. More specifically, FIG. 6 depict an integrated sensor including a single electrolyte tube having two sensing electrodes on the outside of the tube—namely, a $NO_x$ sensing electrode 22 and an $O_2$ sensing electrode 26—along with a single reference electrode 30 inside of the tube. Included within the same housing 24 are the input assembly 12 and a heating device, e.g., an internal dual-zone heating rod 28 shown in FIG. 6. Such a configuration is capable of performing in gas environments with rapidly changing oxygen concentrations.

An oxygen ion conducting electrolyte membrane may be used for both the oxygen sensor 26 and the $NO_x$ sensor 22. To improve performance, the oxygen sensor 26 may be located within an environment having a different temperature than the environment wherein the $NO_x$ sensor 22 resides. The different heating areas may be accomplished by inserting a heating rod 28 inside of a ceramic electrolyte tube, wherein the heating rod shown in FIG. 6 is constructed with two separate heating zones. Alternatively, a single temperature heating rod can be utilized and the design of the insulation can be modified to control the heat loss to create two different temperature zones; or, a heater external to the sensing element can be implemented to produce the desired temperature zones. Preferred performance of the present invention is achieved when the temperature proximate the $NO_x$ sensor 22 is accurately controlled to 450–550° C. and the temperature proximate the oxygen sensor 26 and the input assembly 12 are maintained at 700–800° C. This results in a rapid response of the oxygen sensor 26 and maximum efficiency of the input assembly 12.

An additional aspect of the $NO_x$ sensor 22 design may include the sensor tip protruding approximately one inch into the exhaust gas stream—thereby adhering to the design principles utilized in the widely used lambda oxygen sensor. This configuration facilitates maintaining two distinct temperature zones between the $NO_x$ sensor 22 portion of the ceramic tube outside of the exhaust manifold and within the sensor body housing—thereby creating enough distance from the oxygen sensor 26 so that the two different temperature zones can be effectively achieved.

Located near the $NO_x$ sensor 22 electrode is a gas exit port comprising a small diameter stainless steel tube that when connected to some type of suction device (not shown), will draw the exhaust gas stream through the porous input assembly 12, past the oxygen sensor electrode 26, past the $NO_x$ sensor 22 electrode, and exiting the housing 24. The suction device can be a small air pump, or the gas suction can be accomplished using the vacuum lines commonly implemented in internal combustion engines. It is also contemplated that that the gas suction can be connected to the exhaust gas recirculation system found in newer types of automobiles. Alternatively, the housing 24 can be designed so that a portion of the exhaust gas stream is diverted into the sensor housing thereby passing through the input assembly 12 to the sensing electrode 22. This variation may be achieved by various hole patterns in the tubular sheathing that is part of the metal housing 24.

It is to be understood that although the preferred embodiments shown here are based on a tubular geometry design, the concepts that enable the apparatus to perform accurately can also be extended to other design components such as a flat plate ceramic multilayer package design, a single electrolyte disk type design, and so forth.

To further facilitate the understanding of the present invention, several exemplifications of the present invention are provided. It is to be understood that the present invention is not limited to these exemplifications.

EXAMPLE 1

A $NO_x$ sensor 22 having a structure of the kind shown in FIG. 2 was constructed of a tubular electrolyte body fabricated by the addition of a binder to a commercially available 8 mole % $Y_2O_3$ doped zirconia powder. The binder/powder mixture was dispensed into a tooling followed by isostatic pressing at 25,000 psi. The ceramic portion was machined to final dimensions and then sintered at 1475° C. for two (2) hours. Next, the ceramic electrolyte was coated with electrodes. The inside of the tube along with a stripe on the outside of the tube (current collector) were coated with a platinum paste electrode material followed by firing at 1000° C. for one (1) hour. Then, the tip of the tube was coated with a tungsten oxide/zirconia mixture that contacted the platinum stripe current collector so that electrical contact was made. The electrode coating was dried and fired at high temperature to promote good adhesion.

The input assembly 12 was fabricated by using a ⅜" diameter stainless steel tube as the housing 24. On the gas exit end of the tube, a silver mesh plug was installed by press fitting the plug into the end of the tube. On the upstream gas flow side of the silver plug, 0.5 grams of ruthenium oxide powder was inserted into the stainless steel tube. This powder was lightly compacted by using a rod to press the powder against the surface of the silver mesh plug. Next, 1.0 gram of CaO powder was inserted into the tube and again a rod was used to lightly compact this powder against the ruthenium oxide powder. Finally, a piece of nickel mesh screen was pressed into the tube and compacted against the CaO powder to keep the powders in place.

The apparatus was tested wherein a gas stream would flow first through the input assembly 12 and then to the $NO_x$ sensor electrode. Gases were mixed together using a four-channel mass flow controller system that enabled changing the $NO_x$ concentration in the gas stream and measuring the sensor voltage signal. A typical voltage response curve generated by varying the $NO_x$ concentration between 50–1000 ppm total $NO_x$ is shown in FIG. 3.

EXAMPLE 2

A $NO_x$ sensor fabricated as described in Example 1 was tested at low concentrations of $NO_x$ gases to demonstrate the low range capability of the present invention. Gases were mixed together using a four-channel mass flow controller system that enabled changing the $NO_x$ concentration in the gas stream and measuring the sensor voltage signal. A certified gas cylinder with a concentration of 20 ppm NO/balance nitrogen was used for this test. The concentration was varied by mixing this gas cylinder with gases from a nitrogen and oxygen cylinder. The concentration was varied in increments of 1 ppm from 1–20 ppm. A graph showing the voltage output signal as a function of $NO_x$ concentration is shown in FIG. 4.

EXAMPLE 3

Figure 5:
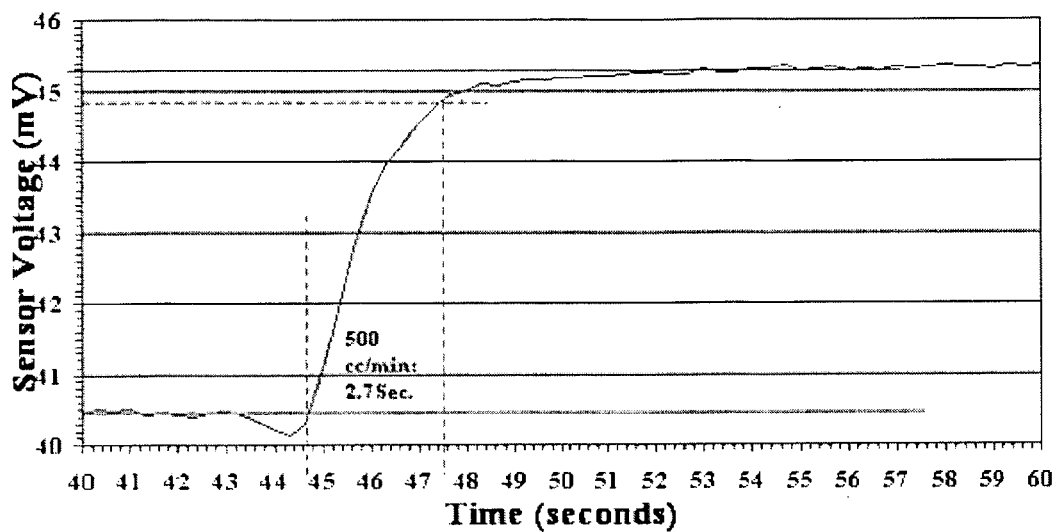
FIG. 5 is a graph showing the response time signal of a $NO_x$ sensor when the $NO_x$ concentration is varied from 470 ppm to 940 ppm; and, FIG. 6 is schematic diagram of one embodiment of the present invention depicting an integrated sensor including a single electrolyte tube with two sensing electrodes on the outside of the tube, namely, a $NO_x$ sensing electrode and an $O_2$ sensing electrode, along with a single reference electrode on the inside of the tube—included within a housing is the input assembly and heater(s), i.e., an internal dual-zone heating rod.

The $NO_x$ sensor fabricated as described in Example 1 was also tested for sensor response time to demonstrate the apparatus' ability to function as part of a control system in a $NO_x$ removal device. Gases were mixed together using a four-channel mass flow controller system that enabled changing the $NO_x$ concentration in the gas stream and measuring the sensor voltage signal. The gas concentration was switched between 470 ppm and 940 ppm $NO_x$ at a flow rate of 500 cc/min. The voltage signal was monitored continuously using a data acquisition system with a sampling rate of three readings per second. The sensor response time is defined as a 90% step change of the total voltage signal when the concentration of the $NO_x$ gas is changed. A sensor response time curve is shown in FIG. 5 that indicates a sensor response time of 2.7 seconds when the $NO_x$ gas concentration is changed from 470 ppm to 940 ppm.

EXAMPLE 4

A combined $NO_x$ and oxygen sensor was fabricated as shown in FIG. 6. A tubular electrolyte body was fabricated by addition of binder to a commercially available 8 mole % $Y_2O_3$ doped zirconia powder. The binder/powder mixture was dispensed into a tooling followed by isostatic pressing at 25,000 psi. The ceramic part was machined to its final dimensions and then sintered at 1475° C. for two (2) hours. Next, the ceramic electrolyte was coated with electrodes. The inside of the tube—along with two stripes on the outside of the tube (current collectors) and the oxygen sensing electrode on the tip—were coated with a platinum paste electrode material followed by firing at 1000° C. for one (1) hour. Then, a 1 cm by 1 cm patch on the side of the tube was coated with a tungsten oxide/zirconia mixture that slightly overlapped the platinum stripe current collector so that electrical contact was made. The electrode coating was dried at 80° C. followed by firing at high temperature to promote adhesion.

The input assembly was fabricated by using a ⅜" diameter stainless steel tube as the housing. On the gas exit end of the tube, a silver mesh plug was installed by press-fitting the plug into the end of the tube. The silver mesh plug was fabricated by cutting twenty-five 0.30" diameter pieces of eighty (80) mesh silver screen and spot welding them together to form a compact plug. On the upstream gas flow side of the silver plug, 0.5 grams of ruthenium oxide powder was inserted into the stainless steel tube. This powder was lightly compacted by using a rod to press the powder against the surface of the silver mesh plug. Finally, a piece of nickel mesh screen was pressed into the tube and compacted against the $RuO_2$ powder to keep the powder in place.

While specific embodiments of the present invention have been illustrated and described, numerous modifications come to mind without significantly departing from the spirit of the invention, and the scope of protection is only limited by the scope of the accompanying claims.

What is claimed is:

1. An apparatus for determining $NO_x$ concentration of an exhaust gas, the apparatus comprising;
   an input assembly capable of receiving the exhaust gas and producing a conditioned output gas, the input assembly including at least three of the following four stages:
   a first stage including a first catalyst structure for converting $NH_3$ in the exhaust gas to $N_2$ and $H_2O$, the first catalyst structure comprising a catalyst material from the group consisting of Cu, Ag, $NiAl_2O_4$, $MnO_2$, $V_2O_5$, and any mixture thereof;
   a second stage including a second catalyst structure having an absorbent material for absorbing $SO_2$ or $H_2S$ from the exhaust gas;
   a third stage including a third catalyst structure for oxidizing unburned hydrocarbons and gases to higher oxidation states; and,
   a fourth stage including a fourth catalyst structure for establishing a steady state equilibrium concentration ratio between NO and $NO_2$; and,
   a $NO_x$ sensor operably connected to the input assembly and receiving the conditioned output gas of the input assembly wherein the concentration of the total $NO_x$ present can be determined.

2. The apparatus of claim 1 wherein the $NO_x$ sensor includes a mixed potential sensor for receiving the conditioned output gas and generating a voltage signal that is a function of the concentration of the total $NO_x$ present.

3. The apparatus of claim 2 further comprising an oxygen sensor, wherein the oxygen sensor and the mixed potential sensor cooperate to determine the $NO_x$ concentration in the exhaust gas.

4. The apparatus of claim 3 wherein the mixed potential sensor and the oxygen sensor are constructed of an electrolyte material.

5. The apparatus of claim 2 wherein the mixed potential sensor includes an electrolyte.

6. The apparatus of claim 5 wherein the electrolyte of the mixed potential sensor is tubular.

7. The apparatus of claim 5 wherein the electrolyte of the mixed potential sensor is planar.

8. The apparatus of claim 2 wherein the mixed potential sensor includes a sensing electrode.

9. The apparatus of claim 8 wherein the sensing electrode of the mixed potential sensor is a semi-conductive oxide material.

10. The apparatus of claim 9 wherein the semi-conductive oxide material includes at least one of the following: $WO_3$, $Cr_2O_3$, $Mn_2O_3$, $Fe_2O_3$, $TiO_2$, $CO_3O_4$.

11. The apparatus of claim 8 wherein the sensing electrode of the mixed potential sensor is a multi-component oxide material.

12. The apparatus of claim 11 wherein the multi-component oxide material is a spinel or perovskite.

13. The apparatus of claim 12 wherein the multi-component oxide material includes at least one of the following: $NiCr_2O_4$, $ZnFe_2O_4$, $CrMn_2O_4$, $LaSrMnO_3$, $LaSrCrO_3$, $LaSrFeO_3$.

14. The apparatus of claim 8 wherein the sensing electrode of the mixed potential sensor is a metallic material.

15. The apparatus of claim 14 wherein the metallic material includes at least one of the following: Pt, Ag, Au, Rh.

16. The apparatus of claim 2 wherein the mixed potential sensor includes a metallic sensing electrode, the metallic sensing electrode includes an electrolyte material having a range of approximately 10–40 vol. %.

17. The apparatus of claim 16 wherein the electrolyte material is approximately 15–25 vol. %.

18. The apparatus of claim 16 wherein the electrolyte material comprises a doped zirconia material, or one of the following: ceria, gadolinia, hafnia, thoria, bismuth oxide, or any mixture thereof.

19. The apparatus of claim 1 wherein the input assembly resides within an environment having a first temperature, the first temperature being above 300° C.

20. The apparatus of claim 19 wherein the first temperature is between 650–750° C.

21. The apparatus of claim 1 further comprising:
a housing wherein the input assembly and the $NO_x$ sensor are housed within the housing.

22. The apparatus of claim 21 wherein the housing is tubular.

23. The apparatus of claim 21 further comprising:
an oxygen sensor housed within the housing, the oxygen sensor residing within an environment having a second temperature.

24. The apparatus of claim 23 wherein the first temperature and the second temperature are different.

25. The apparatus of claim 23 further comprising:
a heating device affixed within the housing and including a first and second heating zone, wherein the first and second heating zones provide the environments having the first and second temperatures, respectively.

26. The apparatus of claim 25 wherein the heating device is a rod.

27. The apparatus of claim 23 further comprising:
a heating device affixed within the housing; and,
an insulation assembly being positioned about the heating device so as to construct a first heating zone and a second heating zone.

28. The apparatus of claim 23 wherein the $NO_x$ sensor resides within an environment having a temperature between 300–700° C. and the oxygen sensor and input assembly reside within an environment having a temperature of at least 500° C.

29. The apparatus of claim 1 wherein the second catalyst structure comprises an absorbing material selected from the group consisting of: CaO, MgO, a perovskite type material, or any mixture thereof.

30. The apparatus of claim 1 wherein the third catalyst structure comprises an oxidizing catalyst material capable of oxidizing CO to $CO_2$, $H_2$ to $H_2O$, and hydrocarbons to $H_2O$ and $CO_2$.

31. The apparatus of claim 30 wherein the oxidizing catalyst material includes $RuO_2$, Pt, Ni, Ag, $CoO_2$, or any mixture thereof.

32. The apparatus of claim 1 wherein the fourth catalyst structure comprises Ag, Pt, Pd, Rh, $RuO_2$, or any mixture thereof.

33. The apparatus of claim 1 wherein each stage of the input assembly resides within an environment having a temperature, and wherein at least two stages of the input assembly reside within an environment wherein the temperatures are different.

34. The apparatus of claim 1 wherein the first stage of the input assembly resides within an environment having a temperature range of approximately 200–500° C.

35. The apparatus of claim 34 wherein the first stage of the input assembly resides within an environment having a temperature range of approximately 250–400° C.

36. The apparatus of claim 1 wherein the second stage of the input assembly resides within an environment having a temperature range of approximately 200–900° C.

37. The apparatus of claim 36 wherein the second stage of the input assembly resides within an environment having a temperature range of approximately 600–800° C.

38. The apparatus of claim 1 wherein the third stage of the input assembly resides within an environment having a temperature range of approximately 200–900° C.

39. The apparatus of claim 38 wherein the third stage of the input assembly resides within an environment having a temperature range of approximately 600–800° C.

40. The apparatus of claim 1 wherein the fourth stage of the input assembly resides within an environment having a temperature range of approximately 200–900° C.

41. The apparatus of claim 40 wherein the fourth stage of the input assembly resides within an environment having a temperature range of approximately 600–800° C.

42. The apparatus of claim 1 further comprising:
an oxygen ion conducting electrolyte including a conducting membrane having a first and a second side, wherein the first side includes a reference electrode capable of being controlled by a known gas concentration or a chemical potential, and the second side being exposed to the conditioned output gas of the input assembly.

43. The apparatus of claim 42, wherein the known gas concentration is atmospheric air.

44. The apparatus of claim 42 wherein the oxygen ion conducting electrolyte comprises a doped zirconia material, or one of the following: ceria, gadolinia, hafnia, thoria, bismuth oxide, or any mixture thereof.

45. The apparatus of claim 1 further comprising:
an oxygen sensor; and,
an electronic system utilizing a formula and capable of calculating the $NO_x$ concentration of the exhaust gas based on a measured oxygen concentration and on output voltage signal from the $NO_x$ sensor.

46. The apparatus of claim 1 further comprising:
an oxygen sensor; and,
an electronic system and a database including a data table or a formula describing a mathematical relationship, wherein the electronic system, database, formula, or data table cooperate to determine the $NO_x$ concentration of the exhaust gas as a function of oxygen concentration.

47. The apparatus of claim 46 wherein the oxygen sensor resides within an environment having a temperature of approximately 400–900° C.

48. The apparatus of claim 47 wherein the temperature range is approximately 600–800° C.

49. The apparatus of claim 1 wherein the input assembly is stable in $H_2O$ containing gases.

50. A method for determining total $NO_x$ concentration is a gas composition, the method comprising the steps of:
receiving an exhaust gas stream;
conditioning the exhaust gas stream through and input catalyst assembly, the input assembly comprising at least three of the following stages:
a first stage for converting $NH_3$ compounds to $N_2$ and $H_2O$, the first stage comprising a catalyst material from the group consisting of Cu, Ag, NiAl$_2$O$_4$, MnO$_2$, V$_2$O$_5$, any mixture thereof;

a second stage for absorbing SO$_2$ form the exhaust stream to improve the lifetime performance of the sensor by minimizing any long term poisoning effects associated with SO$_2$;

a third stage for oxidizing unburned hydrocarbons and oxidized gases to higher oxidation states; and, a fourth stage for establishing a steady state equilibrium concentration ratio between NO and NO$_2$; and, generating a voltage signal that is a function of the concentration of the total NO$_x$ present in the exhaust gas stream.

51. The method of claim 50 further comprising the steps of:

providing an oxygen sensor; and, providing a first heating zone and a second heating zone, the first heating zone being positioned proximate the mixed potential sensor and the second heating zone being proximate the oxygen sensor.

52. The method of claim 51 further comprising the steps of;

heating the first heating zone; and, heating the second heating zone, wherein the first and second heating zones include different temperatures.

53. The method of claim 52 wherein the temperature of the first heating zone is at least 300° C. and the temperature of the second heating zone is at least 500° C.

54. An apparatus for determining NO$_x$ concentration of an exhaust gas, the apparatus comprising;

an input assembly capable of receiving the exhaust gas and producing a conditioned output gas, the input assembly comprising, a first stage including a first catalyst structure having an absorbent material for absorbing SO$_2$ or H$_2$S from the exhaust gas;

a second stage including a second catalyst structure for oxidizing unburned hydrocarbons and gases to higher oxidation states; and, a third stage including a third catalyst structure for establishing a steady state equilibrium concentration ratio between NO and NO$_2$; and, a NO$_x$ sensor operably connected to the input assembly and receiving the conditioned output gas of the input assembly wherein the concentration of the total NO$_x$ present can be determined.

55. The apparatus of claim 54, wherein the NO$_x$ sensor includes a mixed potential sensor for receiving the conditioned output gas and generating a voltage signal that is a function of the concentration of the total NO$_x$ present.

56. The apparatus of claim 54, further comprising:

a heating device affixed within the housing; and, an insulation assembly being positioned about the heating device so as to construct a first heating zone and a second heating zone.

57. The apparatus of claim 54, wherein the NO$_x$ sensor resides within an environment having a temperature between 300–700° C. and the oxygen sensor and input assembly reside within an environment having a temperature of at least 500° C.

58. The apparatus of claim 54, wherein the NO$_2$ concentration in the steady state equilibrium ratio is between about 0% an about 10% by volume.

59. An apparatus for determining NO$_x$ concentration of an exhaust gas, the apparatus comprising;

an input assembly capable of receiving the exhaust gas and producing a conditioned output gas, the input assembly including at least three of the following four stages:

a first stage including a first catalyst structure for converting NH$_3$ in the exhaust gas to N$_2$ and H$_2$O;

a second stage including a second catalyst structure having an absorbent material for absorbing SO$_2$ or H$_2$S from the exhaust gas;

a third stage including a third catalyst structure for oxidizing unburned hydrocarbons and gases to higher oxidation states; and, a fourth stage including a fourth catalyst structure for establishing a steady state equilibrium concentration ratio between NO and NO$_2$, said NO$_2$ concentration between about 0% an about 10% by volume; and, a NO$_x$ sensor operably connected to the input assembly and receiving the conditioned output gas of the input assembly wherein the concentration of the total NO$_x$ present can be determined.

60. The apparatus of claim 59, wherein the NO$_x$ sensor includes a mixed potential sensor for receiving the conditioned output gas and generating a voltage signal that is a function of the concentration of the total NO$_x$ present.

61. The apparatus of claim 59, further comprising:

a heating device affixed within the housing; and, an insulation assembly being positioned about the heating device so as to construct a first heating zone and a second heating zone.

62. The apparatus of claim 59, wherein the NO$_x$ sensor resides within an environment having a temperature between 300–700° C. and the oxygen sensor and input assembly reside within an environment having a temperature of at least 500° C.

63. The apparatus of claim 59, wherein the first catalyst structure comprising a catalyst material from the group consisting of Cu, Ag, NiAl$_2$O$_4$, MnO$_2$, V$_2$O$_5$, WO$_3$ and any mixture thereof.

64. An apparatus for determining NO$_x$ concentration of an exhaust gas, the apparatus comprising;

an input assembly capable of receiving the exhaust gas and producing a conditioned output gas, wherein said input assembly is not surrounded by or substantially enclosed by one or more oxygen ion conductors, the input assembly including at least three of the following four stages:

a first stage including a first catalyst structure for converting NH$_3$ in the exhaust gas to N$_2$ and H$_2$O, the first catalyst structure comprising a catalyst material from the group consisting of Cu, Ag, NiAl$_2$O$_4$, MnO$_2$, V$_2$O$_5$, WO$_3$, and any mixture thereof;

a second stage including a second catalyst structure having an absorbent material for absorbing SO$_2$ or H$_2$S from the exhaust gas;

a third stage including a third catalyst structure for oxidizing unburned hydrocarbons and gases to higher oxidation states; and, a fourth stage including a fourth catalyst structure for establishing a steady state equilibrium concentration ratio between NO and NO$_2$; and a NO$_x$ sensor operably connected to the input assembly and receiving the conditioned output gas of the input assembly wherein the concentration of the total NO$_x$ present can be determined.

65. The apparatus of claim 64, wherein the NO$_x$ sensor includes a mixed potential sensor for receiving the conditioned output gas and generating a voltage signal that is a function of the concentration of the total $NO_x$ present.

66. The apparatus of claim 64, further comprising:
a heating device affixed within the housing; and,
an insulation assembly being positioned about the heating device so as to construct a first heating zone and a second heating zone.

67. The apparatus of claim 64, wherein the $NO_x$ sensor resides within an environment having a temperature between 300–700° C. and the oxygen sensor and input assembly reside within an environment having a temperature of at least 500° C.

* * * * *